US009678047B2

(12) United States Patent
Gozum

(10) Patent No.: US 9,678,047 B2
(45) Date of Patent: Jun. 13, 2017

(54) DYE COMPOSITIONS

(75) Inventor: John E. Gozum, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 367 days.

(21) Appl. No.: 13/534,035

(22) Filed: Jun. 27, 2012

(65) Prior Publication Data

US 2013/0052741 A1 Feb. 28, 2013

Related U.S. Application Data

(60) Provisional application No. 61/527,888, filed on Aug. 26, 2011.

(51) Int. Cl.
*G01N 21/75* (2006.01)
*G01N 31/22* (2006.01)
*G01N 21/78* (2006.01)

(52) U.S. Cl.
CPC .............. *G01N 31/22* (2013.01); *G01N 21/78* (2013.01)

(58) Field of Classification Search
CPC ........ G01N 21/75; G01N 31/22; G01N 33/84; G01N 33/20; G01N 21/78; G01N 21/29; G01N 21/77; G01N 21/25; A61K 31/295; A61K 31/7016; A61K 33/26
USPC .................................................... 436/84, 73
See application file for complete search history.

(56) References Cited

U.S. PATENT DOCUMENTS

| 5,039,618 | A | 8/1991 | Stone |
| 5,416,028 | A | 5/1995 | Stone |
| 5,550,061 | A * | 8/1996 | Stone .............................. 436/73 |
| 5,558,835 | A | 9/1996 | Kozarsky |
| 5,567,619 | A | 10/1996 | Stone |
| 5,912,180 | A | 6/1999 | Stone |
| 6,225,128 | B1 | 5/2001 | White |
| 6,248,593 | B1 | 6/2001 | Esswein |
| 6,800,485 | B2 | 10/2004 | Cole |
| 2004/0018359 | A1* | 1/2004 | Haggquist ................ 428/402.21 |
| 2007/0031972 | A1 | 2/2007 | Attar |
| 2010/0193244 | A1* | 8/2010 | Hoskins ................ C09K 8/035 175/5 |
| 2010/0305234 | A1* | 12/2010 | Calle et al. .................... 523/205 |

OTHER PUBLICATIONS

3M Glass Bubbles, K Series, S Series 2009.*
Paraffin Products. Properties, Technologies, Applications (p. 117) M. Freund, R. Csikos, S. Keszthelyi, GY Mozes 1983.*
International Search Report, PCT/US2012/050772, mailed Feb. 22, 2013, 3 pages.
Billmeyer, Textbook of Polymer Science; 3rd Edition, 1984, (p. 330).
Nairn, Polymer Structure and Characterization, Fall 2007, (First two chapters).
Pearson, "The Effect of Molecular Weight and Weight Distribution Upon Polymer Melt Rheology", Polymer Engineering and Science, May 1978, vol. 18, No. 7, (pp. 583-589).

* cited by examiner

*Primary Examiner* — Krishnan S Menon
*Assistant Examiner* — Dwan A Gerido
(74) *Attorney, Agent, or Firm* — Kenneth B. Wood

(57) ABSTRACT

Dye compositions comprising rhodizonate dye particles encapsulated within a shearable hydrophobic organic encapsulant composition.

15 Claims, 1 Drawing Sheet

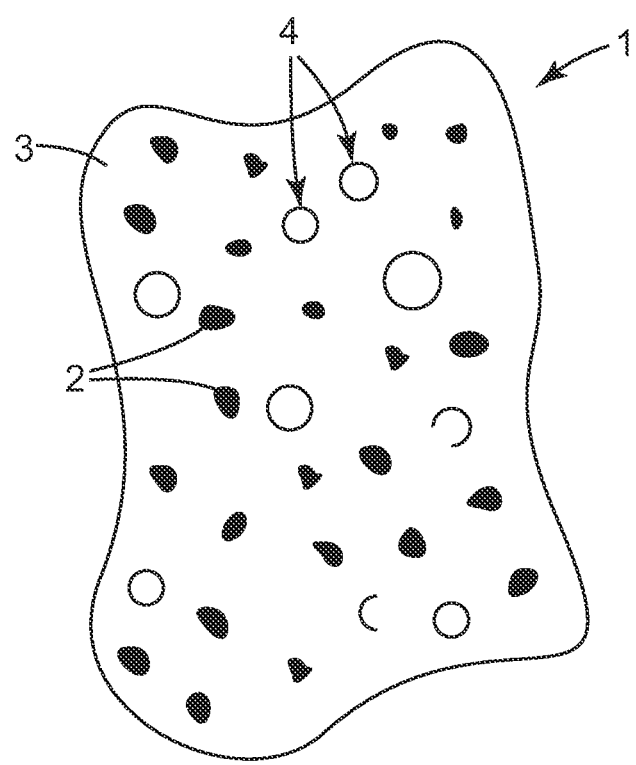

DYE COMPOSITIONS

CROSS REFERENCE TO RELATED APPLICATION

This application claims the benefit of U.S. Provisional Patent Application No. 61/527,888, filed Aug. 26, 2011, the disclosure of which is incorporated by reference herein in its entirety.

BACKGROUND

Rhodizonate dyes are often used as indicators for the detection, e.g. colorimetric detection, of lead.

SUMMARY

Disclosed herein in one aspect are dye compositions comprising rhodizonate dye particles encapsulated within a shearable hydrophobic organic encapsulant composition.

In another aspect, herein is disclosed a kit for detecting lead, comprising: at least one container containing a dye composition comprising rhodizonate dye particles encapsulated within a shearable hydrophobic organic encapsulant composition; and, at least one container containing an acidic buffer solution.

In another aspect, herein is disclosed a method of detecting lead, the method comprising: applying a dye composition comprising rhodizonate dye particles encapsulated within a shearable hydrophobic organic encapsulant composition, to a sample potentially containing lead; and, bringing an acidic buffer solution into contact with the dye composition; wherein the applying of the dye composition to the sample and/or the bringing of the acidic buffer solution into contact with the dye composition is performed in such manner as to manually shear the dye composition and the shearable hydrophobic organic encapsulant composition thereof, so as to release at least some of the rhodizonate dye particles from the encapsulant composition so as to allow at least some rhodizonate molecules to partition into the acidic buffer solution to form a detection mixture.

These and other aspects of the invention will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWING

In the FIGURE is shown an exemplary composition comprising a shearable hydrophobic organic encapsulant, and rhodizonate dye particles, as disclosed herein.

The FIGURE is not to scale and is chosen for the purpose of illustrating exemplary embodiments of the invention. In particular the dimensions of the various components are depicted in illustrative terms only, and no relationship between the dimensions of the various components should be inferred from the drawings, unless so indicated.

DETAILED DESCRIPTION

Shown in the FIGURE is dye composition 1, comprising rhodizonate dye particles 2 encapsulated within a shearable hydrophobic organic encapsulant composition 3. Rhodizonate dyes are often used for detecting e.g. lead, and may be used in any form which is suitable for such purposes. For example, rhodizonate dye particles 2 may be in the form of the disodium salt of rhodizonic acid (CAS number 523-21-7), the potassium salt of rhodizonic acid (CAS number 13021-40-4), etc.

For purposes of detecting e.g. lead, dye composition 1 may be used in combination with a buffer solution in which the rhodizonate is at least partially dissolved at an acidic pH conducive to the detection of lead. However, rhodizonate dyes are somewhat unstable in aqueous solution and their performance may be comprised if packaged in aqueous solution, or even in such conditions that excessive moisture reaches the dye particles. Thus, the inventors have devised a system by which rhodizonate dye may be packaged in a form in which it is protected from water, moisture, etc., but from which it can be easily released when it is desired to combine the dye with an acidic buffer solution to form a detection mixture. (Such an acidic solution is referred to for convenience herein as a "buffer", and may conveniently comprise e.g. a tartrate buffer, but strictly speaking it may not necessarily require a great deal of buffering capacity; e.g. it may simply be an acidic solution, as evidenced in the Examples herein).

As disclosed herein, rhodizonate dye particles 2 are encapsulated within a shearable hydrophobic organic encapsulant composition 3 to form dye composition 1. By shearable encapsulant composition is meant any material or mixture of materials within which the dye particles can be encapsulated such that they are satisfactorily protected from moisture, but from which the dye particles can be released by manual shearing. (Those of ordinary skill will appreciate that the term encapsulated does not necessarily require that every single rhodizonate dye particle is completely surrounded by encapsulant, as long as sufficient numbers of dye particles are sufficiently well protected from moisture to provide the functioning disclosed herein.) In this context, manual shearing means performed by hand by a user (such as by smearing, rubbing, mixing, smashing, etc.), without any mechanized or special equipment except e.g. a spatula or the like. (It will thus be understood that e.g. high molecular weight thermoplastic or thermoset polymers that cannot be manually sheared are not shearable encapsulants). Such manual shearing may occur e.g. during the applying of dye composition 1 onto a sample (e.g. onto a surface of a substrate potentially containing lead), as a precursor step to the applying of dye composition 1 onto the sample, and/or during the bringing of an acidic buffer solution into contact with dye composition 1 and the mixing therewith to form an indicating mixture.

This manual shearing can thus shear at least portions of shearable hydrophobic encapsulant composition 3 such that at least portions of at least some rhodizonate dye particles 2 are released from encapsulant composition 3 and can then come into contact with portions of the acidic buffer solution and dissolve thereinto to form an indicating mixture. In the presence of lead, the indicating mixture may display a color change, which may be optically interrogated (e.g., by visual inspection by a user, by the use of instrumentation, and so on).

The providing of rhodizonate dye particles 2 within an encapsulant composition 3 as disclosed herein may provide advantages over conventional methods of packaging rhodizonate dye e.g. as a dry powder within a hermetically sealed container. For example, the methods disclosed herein may minimize or eliminate the necessity for hermetically sealed packaging, and may make possible many different delivery systems for the dye (e.g., delivery systems which are not limited to one-time use).

In some embodiments, dye composition 1 may be packaged as a kit along with an acidic buffer solution. Dye composition 1 may be provided in a container, although such a container may not necessarily need to be hermetically sealed before an initial use and/or between uses. Dye composition 1 may be applied to a sample by any convenient method, e.g. by removing a small portion of dye composition 1 from the container and then applying the small portion to the sample; or, by directly applying dye composition 1 from the container onto the sample, and so on. The above-mentioned manual shearing of dye composition 1 may be performed at any suitable time, including as a precursor to the applying of dye composition 1 to a sample, and/or during the applying of dye composition 1 to the sample. However, it may be particularly suitable to perform at least a portion of the manual shearing during the act of bringing an acidic buffer solution into contact with dye composition 1 and mixing it therewith to form an indicating mixture. Thus, in some embodiments the manual shearing is performed by manually working (e.g., with a spatula or any other suitable simple tool) a mixture of dye composition 1 and an acidic buffer solution, e.g. by applying them both to a sample surface and stirring the mixture, pressing the mixture against the sample surface, etc. In such manner, the shearable encapsulant may be sheared so as to expose at least portions of at least some rhodizonate dye particles so that they can partition into (i.e., at least partially dissolve into) the buffer solution, as mentioned previously. Those of ordinary skill will appreciate that, e.g. depending on the size and characteristics of rhodizonate dye particles 2 as incorporated into dye composition 1, some shearing, modification in size or shape, breaking up, etc., of rhodizonate dye particles 2 may also occur during the shearing process, which may further enhance the ability of the rhodizonate dye particles to partition into the acidic buffer solution.

In order to enhance the shearing of dye composition 1, it may optionally comprise one or more particulate abrasive additives 4, as shown in exemplary manner in the FIGURE. The term particulate abrasive additive is used broadly, to signify any particles, mixture of different types of particles, etc., which may be added to dye composition 1, and which, upon the manual shearing of dye composition 1, may augment the shearing effect so as to enhance the release of rhodizonate particles 2 from encapsulant composition 3 so that they can partition into the acidic buffer. In some embodiments such particles may be solid and may comprise e.g. inorganic or organic abrasive particles, by which is meant any particles, of any suitable particle size, as are commonly used in the making of sandpaper, scouring articles, and the like. Such particles are often termed "grit", and may include e.g. alumina, silica, and so on. In some embodiments such particles may be hollow and may be e.g. glass bubbles (glass bubbles are often produced by reducing (e.g., by milling) glass to a fine particle size, and heating the glass particles to a temperature in which surface tension causes the particle to assume a spherical shape and in which the high temperature also causes a latent blowing agent in the glass to decompose to form a gas which causes the glass particle to expand to a hollow sphere). Such particles may include both whole (unbroken) glass bubbles and shards and fragments thereof.

It will be noted that particulate abrasive additives do not have to be conventionally "abrasive", and in fact may be chosen from a wide variety of candidates (as long as they do not interfere with the ability of the encapsulate composition to protect the rhodizonate dye from moisture), including particles other than those which are customarily used in sandpaper and the like. It will be further noted that at least some particulate abrasive particles may provide a further advantage in that if dye composition 1 is manually sheared while in contact with a surface of a sample, certain particulate abrasive particles may (in addition to enhancing the releasing of rhodizonate particles 2 from encapsulant composition 3) scratch or abrade the sample surface somewhat which may enhance the liberation of lead (if present) from the sample into a state in which it can be more easily detected. It is thus noted that the presence of one or more particulate abrasive additives may enhance the development of color upon exposure to lead and/or may allow the amount of rhodizonate dye to be minimized.

Shearable hydrophobic organic encapsulant composition 3 is defined as including any suitable material(s) that first, can sufficiently protect rhodizonate dye particles 2 from moisture, e.g. over long-term storage (e.g., up to weeks or months or more) without necessarily being packaged in a hermetically sealed container; and second, can be manually sheared, as described above, so that at least some rhodizonate particles 2 can be released therefrom. (In some embodiments, such release of a rhodizonate dye particle 2 from an encapsulant may amount only to the removal of encapsulant from a limited portion of the surface of the dye particle so as to expose the surface to the acidic buffer, as long as such exposure is sufficient to allow dye molecules to dissolve into the acidic buffer solution to provide satisfactory performance.)

The concept of "organic" embraces any carbon-containing molecule (e.g., containing at least carbon atoms bonded to any of other carbon atoms, hydrogen atoms, and/or silicon atoms, and including e.g. compounds ranging from pure hydrocarbons and derivatives thereof, to compounds containing ether, ester, amide groups or the like, as well as to compounds containing silicone (polysiloxane) groups). Such materials may be derived e.g. from plants, animal, or insect sources, or may be synthesized or derived from sources such as petroleum, natural gas, coal, or the like).

The concept of "manually shearable" embraces any organic material (which may be variously described, e.g. by different vendors, as waxes, greases, lubricants, semi-solids, jellies, and so on) with a hardness value in dmm (measured in the general manner outlined in ASTM Test Method D-5, with dmm denoting penetration distance in tenths of millimeters) of at least about 4.0 at a temperature of approximately 25° C. The inventor has discovered that materials with dmm hardness values in this range (noting that higher values denote softer materials) are typically satisfactorily manually shearable, as evidenced in the Examples herein. In contrast, materials with hardness values below 4.0 dmm at 25° C. are typically not satisfactorily manually shearable, again as evidenced in the Examples herein. In this regard, it is noted that an unsatisfactorily shearable material may not necessarily be so because of any inability to shear the material sufficiently to incorporate and encapsulate the rhodizonate dye particles within the material. The inventor has found that many materials, even if they are too hard for dye particles to be easily incorporated (e.g., mixed) thereinto at room temperature, can be heated to a temperature at which they are soft enough to allow the dye to be incorporated therein. However, such materials may be so hard at ~25° C. that they are not able to be sheared except by very high forces as are not conveniently manually achieved. Since lead testing and the like is often performed under ambient conditions, e.g. room temperature or thereabouts, this inability to be manually sheared at such temperatures may render certain potential encapsulants unsatisfactory for the purposes described herein.

In various further embodiments, the manually shearable organic hydrophobic material may comprise a dmm hardness at 25° C. of at least about 8, at least about 50, at least about 70, or at least about 90. In further embodiments, the manually shearable organic hydrophobic material may comprise a dmm hardness of at most about 100.

The concept of "hydrophobic" encompasses any organic material (which, again, may be variously described, e.g. by different vendors, as waxes, greases, lubricants, semi-solids, jellies, and so on) that is sufficiently hydrophobic as to satisfactorily protect the rhodizonate dye from moisture, e.g. over durations of up to several weeks or months or more. Such capability can be determined e.g. by taking an encapsulated dye and manually shearing it in the presence of an acidic buffer solution, and exposing the thus-formed indicating mixture to a known lead sample and observing whether the dye still exhibits an acceptable optically interrogatable (e.g., visually observable) response to the lead. Extremely hydrophobic materials (e.g. substantially pure-hydrocarbon materials such as polyethylene waxes and the like) have been found by the inventor to be well suited for such purposes. However, it has been found that materials that are not substantially pure hydrocarbons, and that are thus further down the conventional scale of hydrophobicity, may still serve such purposes. For example, it has been found that at least some oxidized polyethylene homopolymers, and at least some ethylene-vinyl acetate copolymers, can serve satisfactorily, as evidenced in the Examples herein.

Moreover, it has been surprisingly found that at least some other materials which may not necessarily be conventionally viewed as hydrophobic, can still serve as hydrophobic organic encapsulant 3. For further example, the above-mentioned oxidized polyethylene homopolymers have an acid number (mg of KOH required to neutralize one gram of material, indicative of e.g. carboxylic acids or the like in the material) of 15. It has also been found that at least some carboxylic acid-containing materials and similar materials (e.g., ethylene-acrylic acid copolymers, and ethylene-maleic anhydride copolymers) with an acid number of up to 200 can serve satisfactorily, as evidenced in the Examples herein. Thus it appears that certain encapsulants can perform satisfactorily in the present application even if they possess a small amount of e.g. carboxylic acids and the like. Thus, in the present context, the term hydrophobic can encompass at least some materials with an acid number of up to 200. (It is noted that one particular material with an acid number of 120, and a dmm hardness of 8, exhibited performance that was slightly less preferred than some of the other materials presented herein, as discussed in the Examples. However, this appeared to be a specific case of this material comprising a somewhat uniquely rubbery composition, which rendered it slightly more difficult to manually shear thus slightly less efficient at releasing the rhodizonate dye. It is not believed that the behavior of this particular material negates the overall behavior and trends with regard to dmm hardness, and hydrophobicity, that are disclosed and discussed herein.)

Materials which are insufficiently hydrophobic to adequately protect the rhodizonate dye from moisture should however be avoided. For example, a polyethylene glycol encapsulant (PEG; ether-terminated; molecular weight 2000) appeared potentially suitable but it was found that maintaining a rhodizonate dye/PEG composition in a 32° C./90% relative humidity environment for approximately 2 weeks resulted in significant inactivation of the dye. Thus, it was judged that this material was insufficiently hydrophobic to serve as a stand-alone encapsulant in the present context. It should be noted however that this finding does not necessarily preclude the use of encapsulants that comprise e.g. other, less hydrophilic polyether moities and/or some number of polyethylene glycol monomer units. For example, it might be possible to use polyethers containing at least some monomer units such as polypropylene glycol, polybutylene glycol and the like and/or containing some small number of polyethylene glycol monomer units.

The issue of hydrophobicity was evaluated in further detail with regard to the presence of organic hydroxyl groups (which would obviously impart some degree of hydrophilicity). Potential advantages which might result from keeping the amount of organic-hydroxyl groups below a certain threshold were demonstrated by the discovery that incorporating hydroxyl-containing organic solvents into the acidic buffer solution appeared to have deleterious effects on the performance of the rhodizonate dye (when brought into contact with the buffer solution and then exposed to lead). Specifically, the inclusion of propylene glycol (a molecule of molecular weight of 76, containing two OH groups) at approximately 50% by weight in the acidic buffer solution resulted in no color change of the dye upon exposure to lead (as described in further detail in the Examples herein). Similarly, the inclusion of tripropylene glycol methyl ether (a molecule of molecular weight of 206, containing one OH group) in the buffer solution resulted in no color change. The inclusion of ethylene glycol butyl ether (a molecule of molecular weight of 119, containing one OH group), resulted in a faint color change (much less than that of the control example with the standard acidic buffer with no organic hydroxyl-containing additives).

Experiments were also done with various solvents which were applied to a known lead-containing (dried) paint to ascertain whether they could soften the paint so as to enhance the detection of lead. Three solvents were evaluated (specifically, were dabbed onto a test area of the lead-painted substrate and held thereon for two minutes, after which a detection mixture comprising 0.1 wt. % dye/encapsulant sample was applied thereto). It was found that a control sample (with no solvent applied to the lead-painted test area) performed best in terms of red color development. It was found that d-limonene (a terpene-based hydrocarbon) performed the next best, although not as well as the control. Next best was dimethyl adipate (a diester solvent). Worst performing was ethyl lactate (a monobasic ester comprising one hydroxyl). It was thus found that not only did the solvents not seem to advantageously soften the paint so as to enhance the detection of lead, they typically had a deleterious effect which appeared to be worsened by the presence of hydroxyl groups (e.g., a greater degree of hydrophilicity).

While not strictly determinative, these examples appear to attest to the advantages of keeping the hydroxyl groups in the organic encapsulant composition below a certain amount in order to obtain best performance. Thus, in various embodiments, organic encapsulant composition 3 comprises less than about 2, less than about 1, less than about 0.5, or less than about 0.25, percent by weight of hydroxyl groups. In some embodiments, shearable hydrophobic organic encapsulant composition 3 is substantially free of hydroxyl groups. It will be understood that substantially free does not preclude the presence of some extremely low amount, e.g. 0.1 wt. % or less, of hydroxyl groups, as may be statistically present in various materials made e.g. in large-scale production processes. It will be further understood that substantially free of hydroxyls is merely a particular embodiment, not a rigid requirement, since, as noted above, it appears that in some encapsulants at least some small amount of hydroxyl groups (e.g., as part of carboxylic acid groups) can be tolerated.

Thus in summary, in some embodiments shearable hydrophobic organic encapsulant composition 3 can be chosen from any sufficiently hydrophobic organic wax, grease, or the like (irregardless of the exact terminology used by a vendor in describing the material) with a 25° C. hardness of at least about 4.0 dmm. If the encapsulant composition comprises e.g. acid groups or the like, it may comprise an acid number of at most about 200. Encapsulant composition 3 may comprise a single material; or, mixtures of materials may be used. Even if a material has been found not to be suitable when used alone, it may still find use (e.g., as an inexpensive diluent; or, as a viscosifier e.g. to thicken a relatively flowable hydrophobic grease, and so on) at a level at which the collective encapsulant composition can perform satisfactorily. In some embodiments, shearable hydrophobic encapsulant composition 3 does not encompass compositions that are provided as latexes, emulsions, dispersions, suspensions, or the like, in water or in any kind of aqueous mixture.

Other components may also be present in encapsulant composition 3. In some embodiments, one or more hydrophobic organic oils may be present. It has been found that some such oils may meet the above-listed criteria of shearability and hydrophobicity (as evidenced in the Examples); however, they may have the drawback of having a viscosity low enough that the rhodizonate dye particles may settle out therein due to gravity. (It will be appreciated that there may not be a firm dividing line between e.g. organic hydrophobic waxes/greases/jellies etc., and organic hydrophobic oils. In the present context an oil is considered to be a fluid which by itself does not comprise sufficient viscosity to keep the dye particles from settling out over e.g. several days of storage; such a threshold is estimated to correspond to a room temperature viscosity of less than about 10 Pa–s.) Such oils may however serve very well (e.g., as diluents) e.g. if combined with a shearable hydrophobic organic wax, grease, or the like. In particular embodiments, suitable oils may include petroleum-derived oils such as mineral oil, natural products such as corn oil and the like, and so on.

Rhodizonate dye particles 2 may be present in dye composition 1 at any suitable amount. (For example, it may be possible to include a particular level of rhodizonate dye in dye composition 1 in order to achieve a desired sensitivity of dye composition 1 to a given level of lead.) In various embodiments, rhodizonate dye particles may comprise from about 0.1 wt. % to about 10 wt. % of dye composition 1. In further embodiments, rhodizonate dye particles 2 may comprise from about 0.2 wt. % to about 2 wt. % of dye composition 1. In some embodiments, dye composition 1 may consist essentially of rhodizonate dye particles 2 and shearable hydrophobic organic encapsulant composition 3. In particular embodiments, dye composition 1 may consist of rhodizonate dye particles 2 and shearable hydrophobic organic encapsulant composition 3.

LIST OF EXEMPLARY EMBODIMENTS

Embodiment 1

A dye composition comprising rhodizonate dye particles encapsulated within a shearable hydrophobic organic encapsulant composition.

Embodiment 2

The dye composition of embodiment 1 wherein the rhodizonate dye particles are chosen from the group consisting of disodium rhodizonate and potassium rhodizonate.

Embodiment 3

The dye composition of any of embodiments 1-2 wherein the shearable hydrophobic organic encapsulant composition comprises a hardness value of at least about 4.0 dmm.

Embodiment 4

The dye composition of any of embodiments 1-3 wherein the shearable hydrophobic organic encapsulant composition comprises a hardness value of at least about 8 dmm.

Embodiment 5

The dye composition of any of embodiments 1-4 wherein the shearable hydrophobic organic encapsulant composition comprises a hardness value of at least about 50 dmm.

Embodiment 6

The dye composition of any of embodiments 1-5 wherein the shearable hydrophobic organic encapsulant composition comprises an acid number of about 200 or less.

Embodiment 7

The dye composition of any of embodiments 1-6 wherein the shearable hydrophobic organic encapsulant composition comprises an acid number of about 15 or less.

Embodiment 8

The dye composition of any of embodiments 1-7 wherein the shearable hydrophobic organic encapsulant composition is chosen from the group consisting of paraffin waxes, polyethylene homopolymers, petroleum jellies, ethylene-vinyl acetates, oxidized polyethylenes, ethylene-acrylic acids, and mixtures and blends thereof.

Embodiment 9

The dye composition of any of embodiments 1-8 wherein the shearable hydrophobic organic encapsulant composition is substantially free of organic hydroxyl groups.

Embodiment 10

The dye composition of any of embodiments 1-9 wherein the shearable composition further comprises at least one hydrophobic organic oil.

Embodiment 11

The dye composition of any of embodiments 1-10 wherein the rhodizonate dye particles comprise from about 0.2 wt. % to about 2 wt. % of the dye composition.

Embodiment 12

The dye composition of any of embodiments 1-11 wherein the composition comprises at least one particulate abrasive additive.

Embodiment 13

The dye composition of embodiment 12 wherein the particulate abrasive additive is chosen from the group consisting of glass bubbles, inorganic grit particles, and organic grit particles.

Embodiment 14

The dye composition of any of embodiments 12-13 wherein the at least one solid particulate abrasive additive comprises from about 5 wt. % to about 50 wt. % of the dye composition.

Embodiment 15

The dye composition any of embodiments 1-14 wherein the composition consists essentially of rhodizonate dye particles and the shearable hydrophobic organic encapsulant composition.

Embodiment 16

The dye composition of any of embodiments 1-14 wherein the composition consists of rhodizonate dye particles and the shearable hydrophobic organic encapsulant composition.

Embodiment 17

A kit for detecting lead, comprising: at least one container containing a dye composition comprising rhodizonate dye particles encapsulated within a shearable hydrophobic organic encapsulant composition; and, at least one container containing an acidic buffer solution.

Embodiment 18

The kit of embodiment 17, wherein the dye composition is the dye composition of any of embodiments 1-16.

Embodiment 19

A method of detecting lead, the method comprising: applying a dye composition comprising rhodizonate dye particles encapsulated within a shearable hydrophobic organic encapsulant composition, to a sample potentially containing lead; and, bringing an acidic buffer solution into contact with the dye composition; wherein the applying of the dye composition to the sample and/or the bringing of the acidic buffer solution into contact with the dye composition is performed in such manner as to manually shear the dye composition and the shearable hydrophobic organic encapsulant composition thereof, so as to release at least some of the rhodizonate dye particles from the encapsulant composition so as to allow at least some rhodizonate molecules to partition into the acidic buffer solution to form a detection mixture.

Embodiment 20

The method of embodiment 19 further comprising optically interrogating the detection mixture.

Embodiment 21

The method of any of embodiments 19-20, wherein the dye composition is the dye composition of any of embodiments 1-16.

Examples

Preparation of Known Lead-Containing Samples

To make a 0.5% by weight lead-containing coating solution, approximately 0.68 g of Lead dichloride were added to 99.32 g of a polyvinyl acetate (PVAc) emulsion obtained from Celanese, Dallas, Tex., under the trade designation RESYN CP1063, followed by shaking on a shaker table for 1 hour. The mixture was coated onto pieces of drywall and allowed to dry for 2 hours in a 49° C. oven. Additionally, pieces of wood trim covered with paint known to contain lead were obtained.

Preparation of Acidic Buffer Solutions

Acidic buffer solution was prepared by combining approximately 1.5 g of glacial acetic acid with approximately 25 cc of deionized water in a 16 oz. glass jar. Additional deionized water was added to bring the total water up to approximately 250 g. The pH of the buffer solution, as measured by pH paper, was approximately 2.5.

Preparation of Rhodizonate/Encapsulant Mixtures

Representative Example

To a small metal can was added 0.2 g rhodizonic acid disodium salt (obtained from Sigma-Aldrich, St. Louis, Mo.) and 9.8 g of a polyethylene homopolymer wax obtained from Honeywell, Morristown, N.J., under the trade designation AC-1702. The can was heated in a 49° C. oven for 20 minutes to allow easy mixing by hand (with a spatula). Mixing was continued until the mixture achieved a uniform dark green color. The result was a mixture of approximately 2.0 wt. % dye in encapsulant.

Variations in Dye/Encapsulant Ratio

Similar samples to the above were made with a dye concentration of approximately 0.5 wt. %, of approximately 0.2 wt. %, and of approximately 0.1 wt. %.

Incorporation of Particulate Abrasive Additives

Dye/encapsulant mixtures at approximately 0.1 wt. % dye were prepared, incorporating approximately 20 wt. % particulate abrasive additive (based on the total weight of the mixture). Three different particulate additives were evaluated. The first was glass bubbles (obtained from 3M Company, St. Paul, Minn., under the trade designation 3M GLASS BUBBLES K-20); the second was 1000 grit silicon carbide abrasive particles (of the type commonly found on many 1000 grit commercially available sandpapers); the third was P120 grade aluminum oxide abrasive particles (of the type commonly found on many P120 grade commercially available sandpapers).

Variations in Encapsulant Composition

Compositions of rhodizonate dye in combination with various other potentially suitable encapsulants were prepared in similar manner to the Representative Example. For convenience, the potentially suitable encapsulants are listed in Table 1 along with their source, although it is noted that some of these correspond to comparative examples, as disclosed in the Results presented later herein.

TABLE 1

| Vendor ID | Item | Vendor |
|---|---|---|
| A-C 1702 | Polyethylene homopolymer | Honeywell |
| A-C 617 | Polyethylene homopolymer | Honeywell |
| A-C 6 | Polyethylene homopolymer | Honeywell |
| Pureline | Petroleum jelly | Oils, Inc. |
| A-C 430 | Ethylene-vinyl acetate copolymer | Honeywell |
| 44,590-8 | Polyethylene glycol-2000 (MW) | Aldrich |
| A-C 6702 | Oxidized polyethylene | Honeywell |
| A-C 629 | Oxidized polyethylene | Honeywell |
| A-C 573P | Ethylene-maleic anhydride copolymer | Honeywell |
| A-C 5120 | Ethylene-acrylic acid copolymer | Honeywell |
| A-C 5180 | Ethylene-acrylic acid copolymer | Honeywell |
| A-C 820A | Polyethylene homopolymer | Honeywell |
| A-C 9 | Polyethylene homopolymer | Honeywell |
| A-C 1814 | Micronized Fischer-Tropsch homopolymer | Honeywell |
| Pure No. 1 | Carnauba wax | Matheson |

Organic Oils

Compositions were prepared with approximately 2.0 wt. % rhodizonate dye in various organic oils. These included mineral oil, corn oil, linseed oil, and glycerol.

Incorporation of Solvents into the Acidic Buffer Solution

Acidic buffer solutions (comprising acetic acid as described above) were prepared containing approximately 50 wt. % of an organic solvent. Three solutions were prepared; one containing propylene glycol, one containing tripropylene glycol, and one containing ethylene glycol butyl ether.

Testing for Ability to Detect Lead

In the case of painted surfaces, a razor blade or utility knife was used to score the surface multiple times in a parallel fashion to the underlying substrate. In the case of the lead-containing PVAc coating, no such scoring was performed. A small amount (ca. 10-100 mg) of a dye/encapsulant composition was applied to an area of the PVAc coating, and/or to the scored area of the painted wood. A cotton swab (Q-TIP® or similar swab) was saturated with the acetic acid buffer solution and was contacted with the dye/encapsulant mixture and was then used to smear/scrub the acidic solution and the wax mixture together to form a detection mixture on the test area of the substrate. The scrubbing was continued for approximately 30 seconds or until a red color developed on the substrate or the swab. (The red color is indicative of a positive test for lead.) If no red color developed, typically a light yellow color would eventually develop (indicating a negative result for lead). If neither a red or light yellow color developed, either increasing the amount of detection mixture used and/or more thoroughly agitating the detection mixture with the swab was performed, until the onset of a light yellow color, indicating a negative result for lead.

Results

Representative Example

The Representative Example (rhodizonate dye at approximately 2.0 wt. % in A-C 1702 polyethylene homopolymer wax) was found to perform very well in detecting lead. The can containing the dye/encapsulant mixture was kept under ambient conditions for several months, and was opened on numerous occasions during this time. No apparent deterioration in the ability of the dye to detect lead was observed during this time.

Variations in Dye/Encapsulant Ratio

The 0.5 wt. % dye mixture was found to display a positive lead test result, with a red color that was somewhat less intense than the (2.0 wt. % dye) Representative Example. The 0.2 wt. % dye mixture also displayed a positive lead test result, but with a red color that was somewhat less intense than the 0.5 wt. % dye mixture. The 0.1 wt. % dye mixture was found to display a very faint positive test result, much less intense than that of the 0.2 wt. % dye mixture.

Incorporation of Particulate Abrasive Additives

The K-20 glass bubbles did not result in a change in the appearance of the dye/encapsulant mixture as formulated. The glass bubbles did result in a slightly higher intensity of the red color being observed upon exposure of the 0.1 wt. % dye mixture (mixed with the acidic buffer solution) to a lead-containing sample. The 1000 grit silicon carbide particles caused the 0.1 wt. % dye/encapsulant mixture to exhibit a more gray color. The silicon carbide particles did result in a noticeably higher intensity of the red color being observed upon exposure of the 0.1 wt. % dye mixture/buffer to a lead-containing sample. The P120 grit aluminum oxide particles caused the 0.1 wt. % dye/encapsulant mixture to exhibit a more gray color, similar to that of the silicon carbide-containing mixture. The aluminum oxide particles did result in a noticeably higher intensity (higher than that resulting from the 1000 grit silicon carbide particles) of the red color being observed upon exposure of the 0.1 wt. % dye mixture/buffer to a lead-containing sample.

Variations in Encapsulant Composition

Samples of various potential encapsulants were tested (all with approximately 2.0 wt. % rhodizonate dye, in combination with acidic buffer) for their ability to allow the detection of lead. Results are shown in Table 2 (with the Representative Example included for reference as Working Example 1). In this table, the ID of each encapsulant is the trade designation from the vendor, as reported in Table 1. The item description is as reported by the vendor. The hardness is as reported by the vendor (as tested under ASTM D-5), if available, unless otherwise noted. The physical form of the sample is as reported by the vendor, except as noted (entries in italics are based on observations by the inventor). The acid number (mg KOH per gram of sample) is as reported by the vendor (as tested under ASTM D-1386), if available, unless otherwise noted. (In one case the vendor reports a saponification number rather than an acid number.) Dashed entries are those for which against no information is available. In particular, it is believed that those samples for which no acid (or saponification) number is provided, comprise little or no measurable acidity. Potential encapsulants which displayed unacceptable results are labeled Comparative Examples. It should be emphasized, however, that such materials might still be optionally added to an encapsulant composition for other purposes, as long as the encapsulant composition comprises at least one or more encapsulants that provide the functions outlined herein.

TABLE 2

| Example | ID | Item | Hardness, dmm | Form | Acid No. | Lead Test Results |
|---|---|---|---|---|---|---|
| Representative (Working 1) | A-C 1702 | PE homopol | 98 | Grease-like | Nil | Acceptable |
| Working 2 | A-C 617 | PE homopol | 7 | Prill/powder | Nil | Acceptable |
| Working 3 | A-C 6 | PE homopol | 4.0 | Prill, powder | Nil | Acceptable |
| Working 4 | Pureline | Petroleum jelly | — | Jelly | — | Acceptable |
| Working 5 | A-C 430 | EVA copol | 70 | Tacky solid | — | Acceptable |
| Working 6 | A-C 6702 | Oxidized PE | 90 | Grease-like | 15 | Acceptable |
| Working 7 | A-C 629 | Oxidized PE | 4.0 | Prill, powder | 15 | Acceptable |
| Working 8 | A-C 573P | Ethylene-maleic anhydride copol | 4.5 | Powder, pastille | 5[1] | Acceptable |
| Working 9 | A-C 5120 | Ethylene-acrylic acid copol | 8 | Prill | 120 | Acceptable[2] |
| Working 10 | A-C 5180 | Ethylene-acrylic acid copol | 50 | Tacky solid | 200 | Acceptable |
| Comparative 1 | A-C 820A | PE homopol | 1.0 | Powder | Nil | Unacceptable |
| Comparative 2 | A-C 9 | PE homopol | 0.5 | Powder | Nil | Unacceptable |
| Comparative 3 | A-C 1814 | Micronized homopol | 1.0 | Powder | Nil | Unacceptable |
| Comparative 4 | Pure No. 1 | Carnauba wax[3] | ~2 | Hard solid | 2-8 | Unacceptable |
| Comparative 5 | 44,590-8 | PEG-2000 | — | Soft waxy solid | — | Unacceptable[4] |

[1]Saponification No., mg KOH/g
[2]Material was observed to have a unique, somewhat rubbery behavior upon shearing
[3]Hardness and acid number for carnauba wax were obtained from literature sources
[4]Appeared potentially acceptable but dye performance deteriorated upon 2 weeks at 32° C./90% RH Organic Oils The above-described organic oils containing rhodizonate dye were held for two weeks at ambient conditions. At the end of this time, the linseed oil composition had solidified into a yellow mass with precipitate and displayed markedly reduced response to lead. The glycerol composition was quite yellow with precipitate and also displayed markedly reduced response to lead. Both of these oils were judged unacceptable. The mineral oil and corn oil compositions displayed good response to lead. However, some settling or precipitation of the dye particles within the oil was observed. It was judged that these oils might not be suitable for use as a sole encapsulant, but they might at least be suitable for including as a component of an encapsulant composition, e.g., in combination with one of the above-discussed encapsulants.

Effect of Incorporating Solvents into the Acidic Buffer Solution

Representative Example dye/encapsulant compositions were applied to known lead-containing substrates after which acidic buffer solutions comprising the above-described organic solvents were applied and mixed with each dye/encapsulant composition. The inclusion of propylene glycol (at approximately 50% by weight) in the acidic buffer solution was found to result in no red color development upon exposure to lead. Similarly, the inclusion of tripropylene glycol methyl ether resulted in no color change. The inclusion of ethylene glycol butyl ether resulted in a faint color change (much less than that of a control example with the standard acidic buffer with no organic hydroxyl-containing additives).

Effect of Applying Solvents to Lead-Containing Samples

Three organic solvents were tested for their effect on lead-containing (dried) paint. Each solvent was dabbed onto a test area of a lead-painted substrate and held thereon for two minutes, after which a detection mixture comprising 0.1 wt. % dye/encapsulant sample was applied thereto). It was found that a control sample (with no solvent applied to the lead-painted test area) performed best in terms of red color development. It was found that d-limonene (a terpene-based hydrocarbon) solvent performed the next best, although not as good as the control. Next best was dimethyl adipate (a diester solvent). Worst performing was ethyl lactate (a monobasic ester comprising one hydroxyl).

The tests and test results described above are intended solely to be illustrative, rather than predictive, and variations in the testing procedure can be expected to yield different results. All quantitative values in the Examples section are understood to be approximate in view of the commonly known tolerances involved in the procedures used. The foregoing detailed description and examples have been given for clarity of understanding only. No unnecessary limitations are to be understood therefrom.

It will be apparent to those skilled in the art that the specific exemplary structures, features, details, configurations, etc., that are disclosed herein can be modified and/or combined in numerous embodiments. All such variations and combinations are contemplated by the inventor as being within the bounds of the conceived invention. Thus, the scope of the present invention should not be limited to the specific illustrative structures described herein, but rather extends at least to the structures described by the language of the claims, and the equivalents of those structures. To the extent that there is a conflict or discrepancy between this specification as written and the disclosure in any document incorporated by reference herein, this specification as written will control.

What is claimed is:

1. A dye composition comprising rhodizonate dye particles encapsulated within a shearable hydrophobic organic encapsulant composition, wherein the shearable hydrophobic organic encapsulant composition exhibits a hardness value of from 4.0 dmm to 100 dmm at a temperature of 25° C. and comprises a material chosen from the group consisting of shearable hydrophobic organic waxes, greases, semi-solids, jellies, and combinations thereof.

2. The dye composition of claim 1 wherein the rhodizonate dye particles are chosen from the group consisting of disodium rhodizonate and potassium rhodizonate.

3. The dye composition of claim 1 wherein the shearable hydrophobic organic encapsulant composition comprises an acid number of about 200 or less.

4. The dye composition of claim 1 wherein the shearable hydrophobic organic encapsulant composition comprises an acid number of about 15 or less.

5. The dye composition of claim 1 wherein the shearable hydrophobic organic encapsulant composition is substantially free of organic hydroxyl groups.

6. The dye composition of claim 1 wherein the rhodizonate dye particles comprise from about 0.2 wt. % to about 2 wt. % of the dye composition.

7. The dye composition of claim 1 wherein the composition consists essentially of rhodizonate dye particles and the shearable hydrophobic organic encapsulant composition.

8. The dye composition of claim 1 wherein the composition consists of rhodizonate dye particles and the shearable hydrophobic organic encapsulant composition.

9. The dye composition of claim 1 wherein at least some of the rhodizonate dye particles are each individually encapsulated within the shearable hydrophobic organic encapsulant composition.

10. The dye composition of claim 1 wherein the composition comprises at least one particulate abrasive additive.

11. The dye composition of claim 10 wherein the particulate abrasive additive is chosen from the group consisting of glass bubbles, inorganic grit particles, and organic grit particles.

12. The dye composition of claim 10 wherein the at least one solid particulate abrasive additive comprises from about 5 wt. % to about 50 wt. % of the dye composition.

13. A kit for detecting lead, comprising:
at least one container containing a dye composition comprising rhodizonate dye particles encapsulated within a shearable hydrophobic organic encapsulant composition, wherein the shearable hydrophobic organic encapsulant composition exhibits a hardness value of from 4.0 dmm to 100 dmm at a temperature of 25° C. and comprises a material chosen from the group consisting of shearable hydrophobic organic waxes, greases, semi-solids, jellies, and combinations thereof;
and,
at least one container containing an acidic buffer solution.

14. A method of detecting lead, the method comprising:
applying a dye composition comprising rhodizonate dye particles encapsulated within a shearable hydrophobic organic encapsulant composition, wherein the shearable hydrophobic organic encapsulant composition exhibits a hardness value of from 4.0 dmm to 100 dmm at a temperature of 25° C. and comprises a material chosen from the group consisting of shearable hydrophobic organic waxes, greases, semi-solids, jellies, and combinations thereof, to a sample potentially containing lead;
and,
bringing an acidic buffer solution into contact with the dye composition;
wherein the applying of the dye composition to the sample and/or the bringing of the acidic buffer solution into contact with the dye composition is performed in such manner as to manually shear the dye composition and the shearable hydrophobic organic encapsulant composition thereof, so as to release at least some of the rhodizonate dye particles from the encapsulant composition so as to allow at least some rhodizonate molecules to partition into the acidic buffer solution to form a detection mixture.

15. The method of claim 14 further comprising optically interrogating the detection mixture.

* * * * *